(12) United States Patent
Gehm et al.

(10) Patent No.: US 8,462,927 B2
(45) Date of Patent: Jun. 11, 2013

(54) SYSTEM AND METHOD FOR PERSONALIZED SERVICES NETWORK CALL CENTER

(75) Inventors: David Gehm, Birch Run, MI (US);
Lynn Zuellig, Frankenmuth, MI (US);
Jonathan Golm, Macomb, MI (US);
John Cesarz, Warren, MI (US)

(73) Assignee: Lutheran Homes of Michigan, Inc., Frankenmuth, MI (US)

( * ) Notice: Subject to any disclaimer, the term of this patent is extended or adjusted under 35 U.S.C. 154(b) by 160 days.

(21) Appl. No.: 13/177,929

(22) Filed: Jul. 7, 2011

(65) Prior Publication Data
US 2012/0008762 A1    Jan. 12, 2012

Related U.S. Application Data

(60) Provisional application No. 61/362,479, filed on Jul. 8, 2010.

(51) Int. Cl.
*H04M 3/42* (2006.01)
*H04M 3/00* (2006.01)

(52) U.S. Cl.
USPC ............. 379/201.01; 379/265.09; 379/265.02

(58) Field of Classification Search
USPC .......................... 379/201.01, 265.02, 265.09
See application file for complete search history.

(56) References Cited

U.S. PATENT DOCUMENTS

2008/0177653 A1* 7/2008 Famolari et al. ................ 705/37
2012/0143862 A1* 6/2012 Jones ............................ 707/732

* cited by examiner

*Primary Examiner* — Rasha Al Aubaidi
(74) *Attorney, Agent, or Firm* — Robert L. Stearns; Dickinson Wright, PLLC

(57) ABSTRACT

A networking system and method for assisting a user. The system includes a call center with a plurality of representatives. The user establishes communication with one of the representatives and communicates a problem to the representative. The representative enters the problem into a database including a plurality of affiliates and affiliate information. The database identifies an assistance category and prioritizes a list of affiliates as a function of the affiliate information, the assistance category and the user's information. The representative and the user then select one of the affiliates, and the representative sends the user's information to the selected affiliate. After the referral, the representative follows up with the user to ensure that the service provided by the affiliate was satisfactory.

14 Claims, 12 Drawing Sheets

Network Call Center Assessment Program

Demographic Data

Home | Categories | Affiliate | Questions | Scales | Users                                    Feedback

Select Caller Scenario
- ☐ Calling for Self
- ☐ Calling for Relative                ☐ Calling for Resident
- ☐ Calling for Friend                  ☐ Calling for General Information
- ☐ Calling for Professional Inquiry

| Caller Information | Lookup Past Caller | Clear Caller Info |

44

First Name
Last Name
Address
City
State          Michigan
Zip
Primary Phone
Alternate Phone
Email                                                    ☐ Will Not Provide

[ Next Step ]   [ End Call without Saving ]

Network Call Center Assessment Program

Select Methods of Affiliate Information Distribution

Home | Categories | Affiliate | Questions | Scales | Users                                       Feedback

| Affiliate Name | Category | Date |
|---|---|---|
| ✓ Affiliate A — 26 | Transportation | |
| Affiliate B | Transportation | |
| Affiliate C | Transportation | |

How will the Affiliate Information be Provided for Affiliate A?
✓ Provided Over the Phone
  Connect Directly
✓ Send Email to Callers Mother    (verifies email address gather if not corrected: - Email Address    Event, or add)
  Send Email to Caller ☐ Will Not Provide

How will the Affiliate Information be Provided for Affiliate A?

First Name
Last Name
Address
City
State           Michigan
Zip
Primary Phone        None
Alternate Phone      None
Email

[ Next Step ] [ Previous Step ]   [ End Call without Saving ]

SYSTEM AND METHOD FOR PERSONALIZED SERVICES NETWORK CALL CENTER

CROSS REFERENCE TO RELATED APPLICATION

This application claims the benefit of U.S. provisional application Ser. No. 61/362,479 filed Jul. 8, 2010, the entire disclosure of the application being considered part of the disclosure of this application, and hereby incorporated by reference.

BACKGROUND OF THE INVENTION

1. Field of the Invention

Aspects of the present invention relate to a call center, and in particular, to a network for a call center that provides personalized services such as health and wellness assessment.

2. Brief Description of the Related Art

The aging population of the United States is growing, and health care costs in the United States exceed one trillion dollars per year. In 1996, spending on health care in the United States exceeded fourteen percent of the Gross Domestic Product. Current health care system costs include annual service to over ninety million people in over five thousand hospital emergency departments. These ninety million or more visits impose an enormous burden on emergency departments. Ambulances on route toward the closest available emergency department are often diverted to other hospitals, sometimes located in another city. The cause of such calamities is multi-factorial and includes: nursing shortages, bed unavailability, and grossly overcrowded, overburdened emergency rooms.

With rising health care costs, it is imperative that health care providers provide health services efficiently and cost effectively. At the same time, the administrative demands of medical record keeping, billing and managing a medical practice have become more burdensome. In particular, health care providers must be thorough and keep detailed records of medical exams to accurately document observations and services that have been provided.

One health care product growing in popularity is a wellness plan. The principal objective of a wellness plan is to keep a patient well. A wellness plan provides a way for a patient to pre-pay or pay on a schedule for medical services. Under a typical plan, the patient is entitled to preventative care services and discounts on other types of medical services. By establishing periodic visits at least once a year, wellness plans enable health problems to be identified and treated early. It is generally understood that the cost of healthcare rises exponentially the longer a health problem is postponed. Thus, wellness plans can drastically reduce healthcare costs by encouraging office visits that help identify and resolve health problems early.

While wellness plans are an effective way to keep patients healthy, they are difficult and costly to administer and promote. As such there is a need for a more effective approach to managing wellness plans and the personalized services that go with them.

Studies show that over 83% of seniors want to stay in their existing home as long as possible rather than move into a smaller home or retirement community. They also recognize that they need to make some changes in order to continue living in their homes. Many of the activities that they used to do on their own will need to be done by others as they age in place. These include things such as personal care, transportation, medication management, home and yard maintenance, meal preparation, etc. Keeping these seniors in their homes is a large part of a good wellness plan and can greatly reduce their overall cost of care. Knowing about and locating all the different providers of these services is difficult for the senior and/or their caregivers. As such there needs to be a single place to contact for help in connecting to good reputable senior focused service organizations.

SUMMARY OF THE INVENTION

Aspects of the present invention overcome these conventional problems and provide a single, centralized place which can be contacted to request help in connecting to good reputable senior focused service organization.

According to an aspect of the present invention, a method of assisting a user includes the step of storing affiliate information for a plurality of affiliates on a database. The method continues with the step of receiving a communication from a user. The method then proceeds with the step of receiving user information and a reason for the communication from the user. Next, the method continues with the step of storing the user information and the reason for the communication into the database. The method then continues with the step of identifying a first assistance category in response to the communication. The method then proceeds with the step of prioritizing a first list of affiliates as a function of the affiliate information of the plurality of affiliates and the first assistance category identified and the user information. After the first list of affiliates is identified, the method continues with the step of selecting at least one affiliate from the list of affiliates. Next, the method continues with the step of sending the user information and the identified first assistance category to the selected affiliate. The method then continues with the step of determining a follow-up communication time. At the follow-up communication time, the method continues with the step of communicating with the user. Finally, the method includes the step of inputting follow-up notes into the database.

Additional features and advantages of the invention will become more apparent from the following detailed description and accompanying drawings.

DETAILED DESCRIPTION OF THE EXEMPLARY EMBODIMENTS

Figure 1:
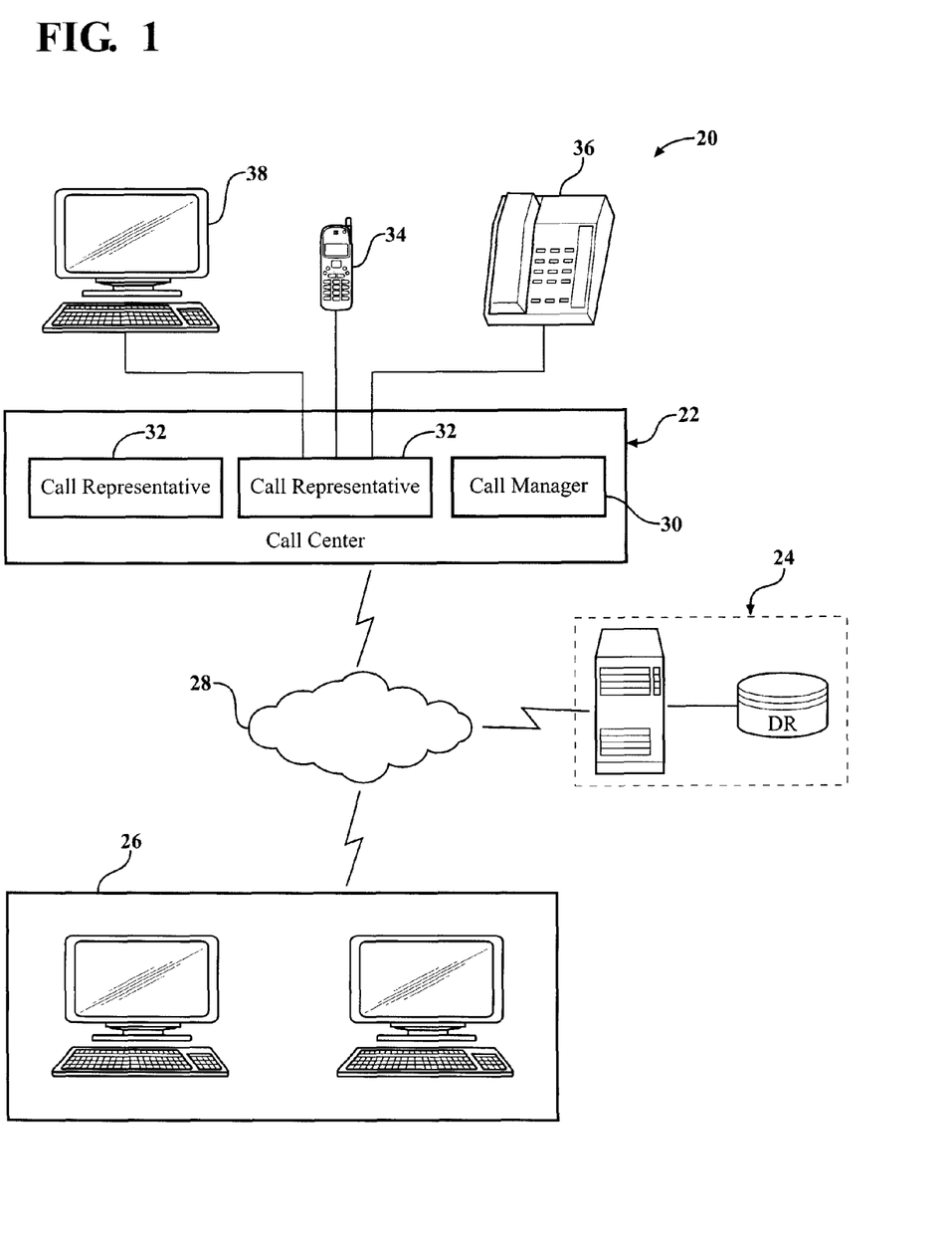
FIG. 1 shows an exemplary call center network in accordance with an embodiment of the invention.

Referring to the Figures, wherein like numerals indicate corresponding parts throughout the several views, a networking system 20 for assisting a user is generally shown in FIG. 1. The networking system 20 includes a call center 22 and a database 24, each of which is connected to the Internet and the public switched telephone network (PSTN) for receiving and transmitting communications with a plurality of users and a plurality of affiliates 26. The Internet and PSTN are collectively illustrated in FIG. 1 as a cloud 28. The database 24 can either be stored locally, i.e. at the call center 22, or it could be located remotely from the call center 22 and accessed through the Internet. The database 24 can be implemented as any combination of hardware and software known to those skilled in the art, for example, the database 24 can include various types of computer readable storage media, such as RAM, EPROM, EEPROM, flash memory, registers, hard disks, CD-ROM, DVD, etc. to store software modules which are configured to perform the tasks described below. The networking system 20 could include a single call center 22 or a plurality of call centers 22 in communication with one another. Alternately, the networking system 20 could include a single call center and a plurality of call center offices, or resource centers, in communication with the call center 22. The call centers could be located in hospitals, churches, nursing homes, assisted living locations or other places where they could reach people in need of assistance.

As will be discussed in greater detail below, the networking system 20 provides users with a place to go for assistance in a very wide range of goods and services. When the user needs assistance, he or she sends a communication to the call center 22, which ultimately routes a request for services to an available affiliate 26 based on a multitude of factors as discussed in further detail below. The services provided by the affiliates 26 could be health care services, community education programs, homemaker services, landscaping services, personal services, etc. Further, the networking system 20 could provide users with a place to go for goods, including for example, medical supplies, groceries, etc.

In the exemplary embodiment, the call center 22 includes a manager 30 and a plurality of representatives 32, and each representative 32 has at least one specialty. The manager 30 receives all communications from the users and directs those communications to the respective representatives 32 according to the subject matter of the communication. For example, the manager 30 could direct a communication related to medical services to a representative 32 who specializes in medical services. It should be appreciated that the representatives 32 do not have to have specialties, and the manager 30 is optional. In such an embodiment, the communications from the users could automatically be conveyed to the representatives 32 according to the availability of the representatives 32. It should also be appreciated that the representatives 32 could either be employees of the call center 22, or the representatives 32 could be a computer program which can automatically communicate with the users.

In the exemplary embodiment, users can communicate with the call center 22 through three different ways. First, users can visit the call center 22 or one of the call center offices and communicate with the manager 30 and representatives 32 in person. Secondly, the users can communicate with the manager 30 and representatives 32 of the call center 22 over the public switched telephone network (PSTN) or over voice over internet protocols (VOIP). It should be appreciated that the user can use either a mobile telephone 34, a landline telephone 36, a computer 38 or any other device to call the call center 22. Thirdly, users can communicate with the manager 30 and representatives 32 over the Internet. The Internet communication could be a web-based online chat session between the user and one of the representatives 32. Alternately, where the representatives 32 are a computer program, the user could respond to a plurality of predetermined questions asked by the computerized representative 32. It is further understood that the above description is not limiting, and that aspects of the present invention encompass a user communicating with the call center 22 using any technology known to those of skill in the art, including, for example, SMS, MMS, etc.

Alternately, the users can let someone else represent them in discussions with the call center 22. The representative could be a family member, a neighbor or a trusted friend. Even further, users could sign up for the networking system 20 in advance and receive an identification card, or some other piece of identification showing their membership in the networking system 20. The user can then give this card to someone else, and thus allowing the other person to communicate with the call center 22 on the user's behalf. For example, a user who is being checked out of a hospital can give his or her identification card to a hospital employee, who will work with the representatives 32 at the call center 22 directly to make sure that the user receives all of the medication and other goods and services that he or she will need at home. This aspect of the networking system 20 is advantageous because it provides the user with the piece of mind of knowing that his or her needs are being taken care of by trained professionals.

The call center 22 represents a source information for the users. Where there is no manager 30, automatic distribution of incoming calls to individual representatives 32 on the networking system 20 begins when a client establishes communication with the call center 22. As explained above, communications from clients to the call center 22 can be accomplished in person, by voice and/or by data. The network system 20 may additionally include web-enabled computer devices for the representatives 32 to communicate with the users and the database 24.

The affiliates 26 are businesses for providing services to the users. Exemplary affiliates 26 could be extended care facilities, rehabilitation facilities, memory care facilities, assisted living communities, independent living communities, affordable housing, certified home care, personal services, hospice, camp hope, etc. As will be discussed in greater detail below, the affiliates 26 are graded by the users who receive the referrals. Therefore, it is important that the affiliates 26 be reliable and punctual. Information about each of the affiliates 26 is stored on the database 24. The affiliate information could be contact information, the location of the affiliate's 26 business, the goods provided by the affiliates 26, the services provided by the affiliates 26, etc.

Figure 2:
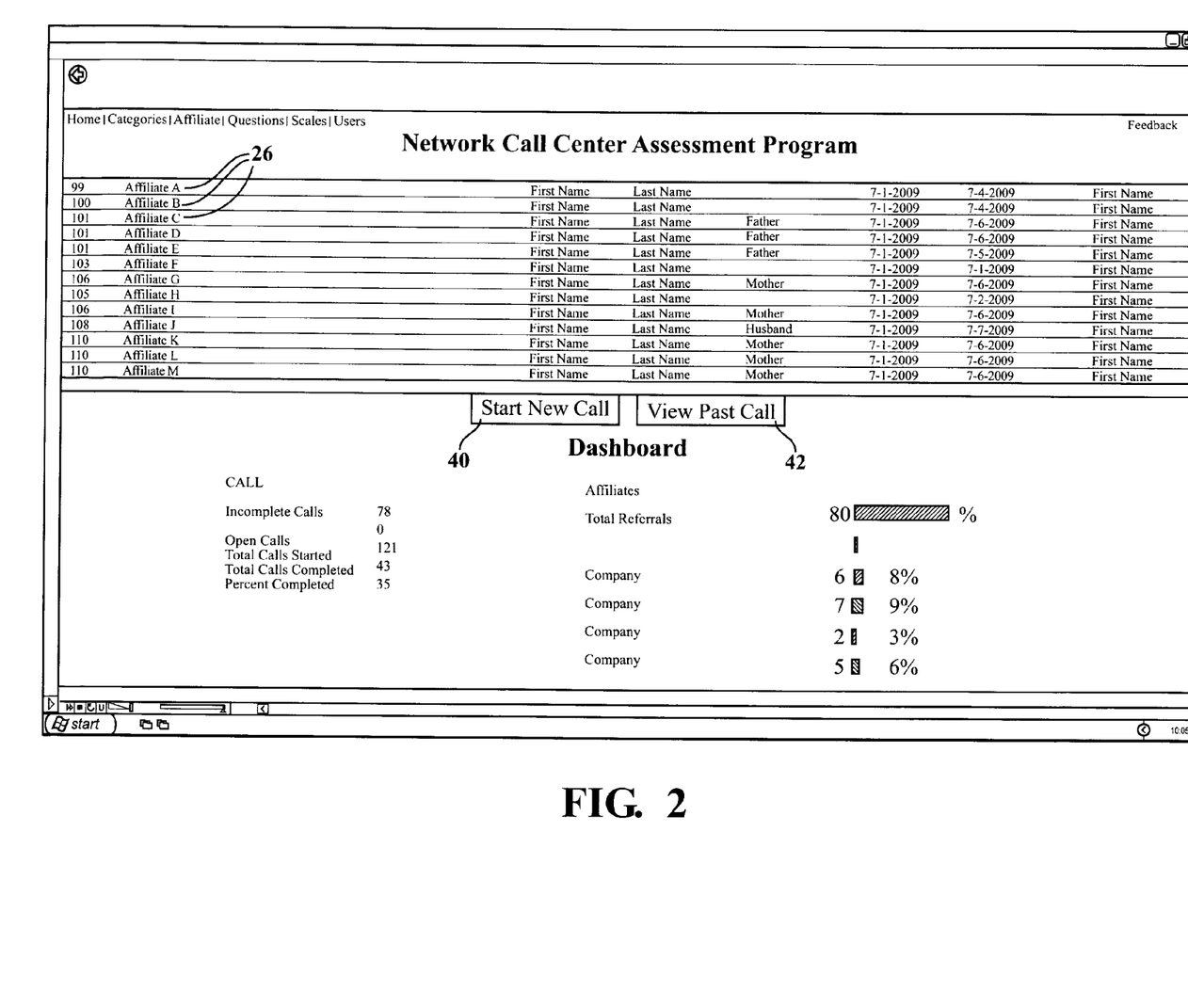
FIG. 2 shows an exemplary Call Center Assessment window of an exemplary computer program for communicating with a database of the call center network.
Figure 3:
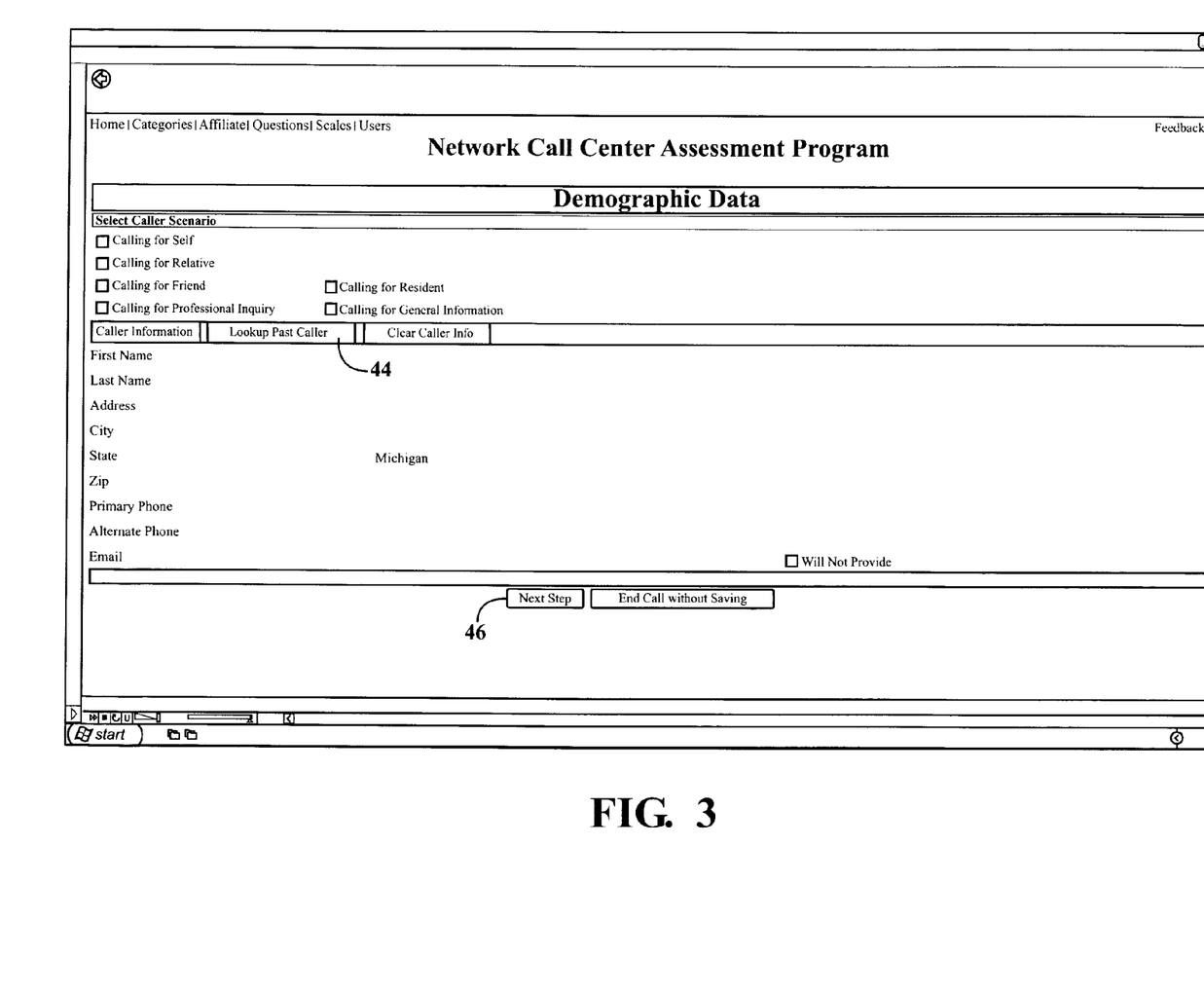
FIG. 3 shows an exemplary Demographic Data window of the exemplary computer program for communicating with the database of the call center network.
Figure 4:
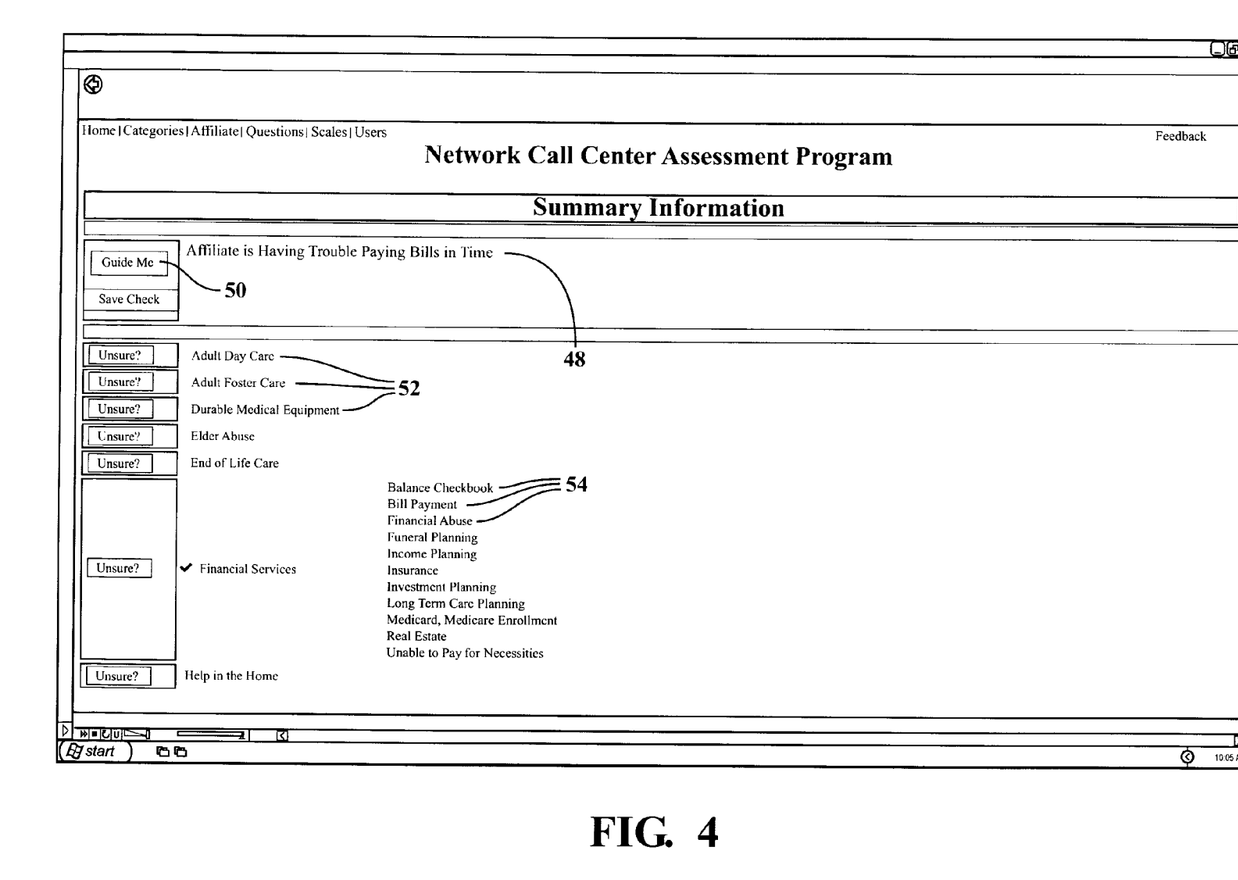
FIG. 4 shows an exemplary Summary Information window of the exemplary computer program for communicating with the database of the call center network.

Referring to FIG. 2, a Call Center Assessment Program window of an exemplary computer program for communicating the database 24 is shown. On this window, the representative 32 can choose an item from a follow-up list, a "Start New Call" link 40 or "View Past Call" link 42. If the representative 32 chooses the "Start New Call" link 40, he or she will be directed to the Demographic Data window shown in FIG. 3. Here, the representative 32 can enter information about the user into the database 24. For example, the representative 32 can enter the capacity of the user, e.g. whether the user is calling for him/herself, a relative, a friend, a professional inquiry, a resident or for general information. On this window, the representative 32 can also enter the user's personal information such as name, address, phone number and email into the database 24. Also included is a "Lookup Past Caller" link 44 for quickly retrieving a past user's personal information. Upon clicking on the "Next Step" link 46, the representative 32 is directed to the Summary Information window shown in FIG. 4.

The exemplary Summary Information window include a box 48 for allowing the representative 32 to enter the reason for the communication from the user. For example, in the exemplary embodiment of FIG. 4, the representative 32 has entered "Mom is having trouble paying bills on time." If the representative 32 clicks the "Guide Me" link 50, then the program automatically presents a plurality of suggested assistance categories 52. For example, the assistance categories 52 could be adult day care, adult foster care, durable medical equipment, etc. The representative 32 can choose one or more of the assistance categories 52, which will then display a plurality of subcategories 54. Upon choosing at least one assistance category 52 and subcategory 54, the representative 32 is directed to the Affiliated Resource Results window shown in FIG. 5. It should be appreciated that the representative 32 could alternately choose only an assistance category and not a subcategory.

Figure 5:
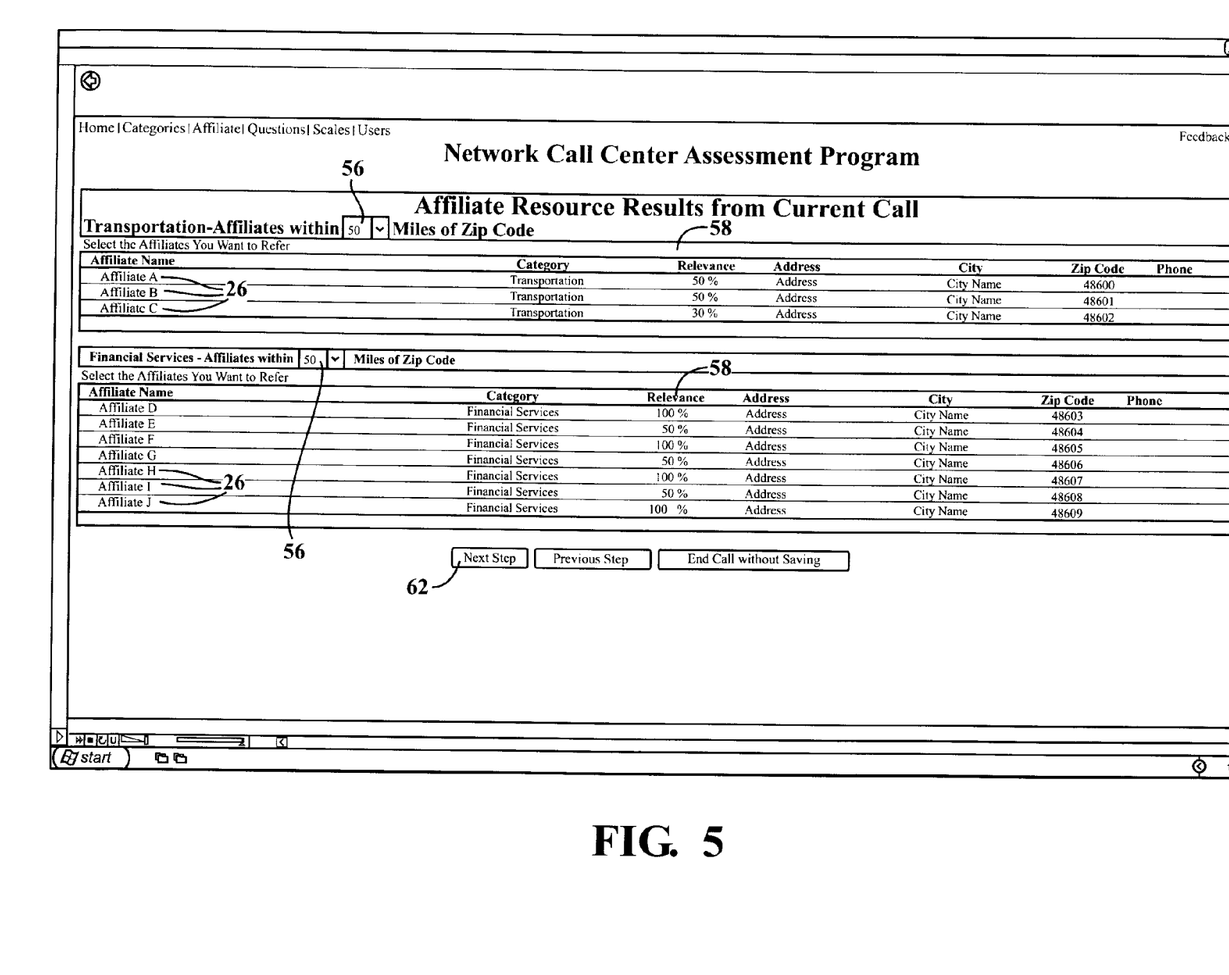
FIG. 5 shows an exemplary Affiliate Resource Results window of the exemplary computer program for communicating with the database of the call center network.

The database 24 creates and presents in the Affiliated Resource Results window a list of affiliates 26 for each of the assistance categories 52 and/or subcategories 54 chosen. The lists are prioritized as a function of the affiliate information; the assistance categories 52 and/or subcategories 54; and the user information. The Affiliated Resource Results window also includes a box 56 for choosing the radius around the user's zip code where the database 24 should display available associates. In other words, the representative 32 can choose to only display, for example, affiliates 26 in the database 24 which are within fifty miles of the user's zip code. The Affiliated Resource Results window also displays a relevance column 58, which presents a score for each of the affiliates 26. As will be discussed in greater detail below, the relevance score can be based, at least partially, on how other users have graded the specific affiliate's 26 previous performance. The relevance score is also preferably based on the services and/or goods provided by the affiliate 26 as compared to the services and/or goods needed by the user according to the assistance category or categories chosen by the representative 32. Also, the relevance score can be based on combinations of different needs requested by the user. For example, if the user requests an affiliate 26 who has expertise in financial assistance services (e.g., "Mom has trouble paying bills on time") as well as an affiliate 26 who has expertise in landscaping services (e.g., "Mom has trouble mowing the lawn") from the representative 32, the relevance score can indicate the relevance of the determined affiliates 26 based on the multiple requested services, for example, by using a percentage indicator (e.g., an affiliate 26 who provides both financial assistance services and landscaping services has a relevance score of 100%, an affiliate who provides only one of financial assistance services or landscaping services has a relevance score of 50%, etc.).

Figure 6:
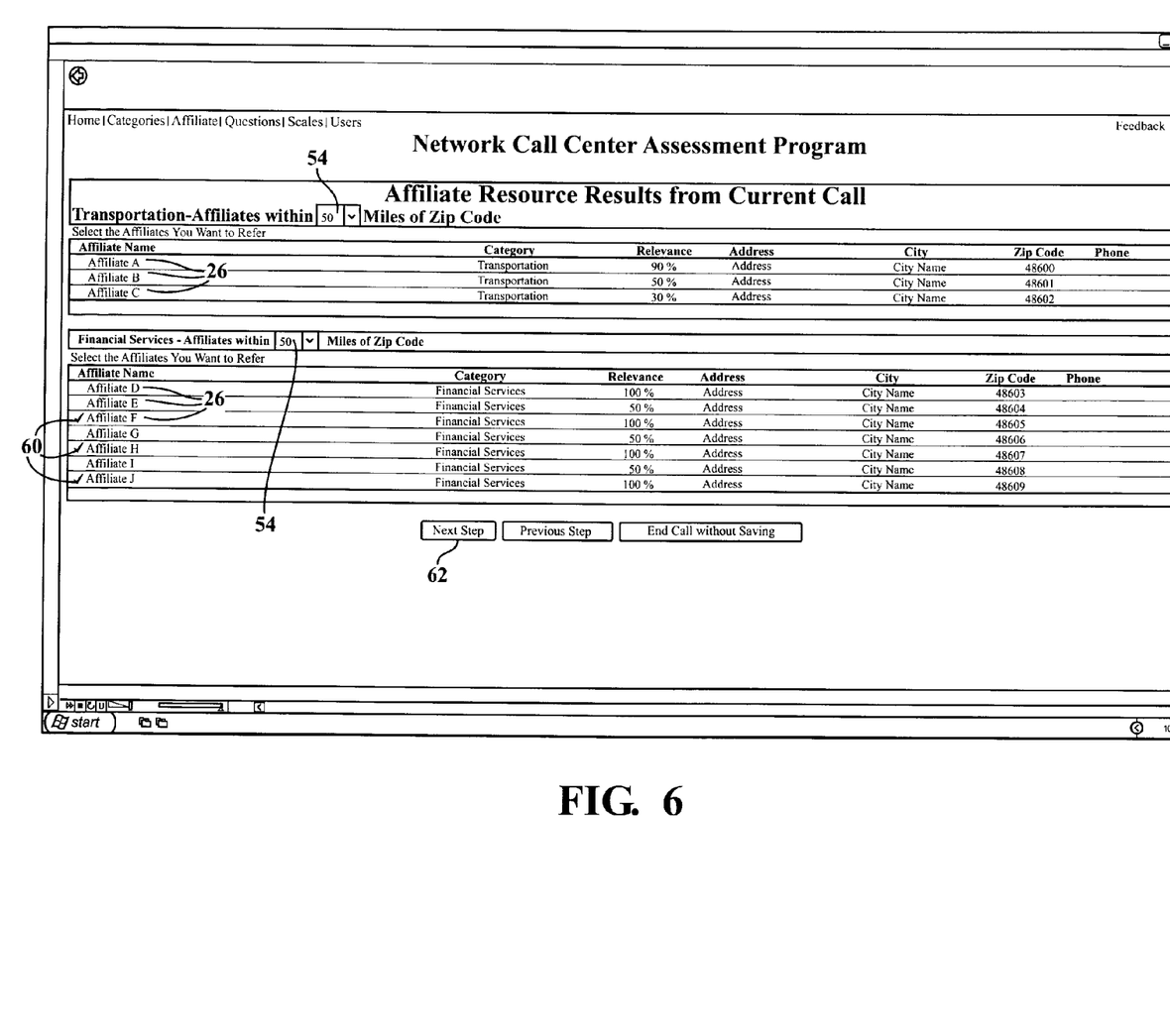
FIG. 6 shows an exemplary Select Methods of Affiliate Information Distribution window of the exemplary computer program for communicating with the database of the call center network.

The representative 32 preferably discusses with the user which of the affiliates 26 to choose. The user can give the representative 32 written or oral confirmation of which affiliates 26 he/she desires to do business with. Once the user has chosen, the representative 32 clicks on the desired affiliates 26. Clicking on the affiliates 26 will cause the Affiliate Resource Results window to present check marks 60 next to the chosen affiliates 26, as shown in FIG. 6. Next, after at least one of the affiliates 26 has been chosen for each of the assistance categories, the representative 32 can click on the "Next Step" link 62 to present the Select Methods of Affiliate Information Distribution window shown in FIG. 7.

Figure 7:
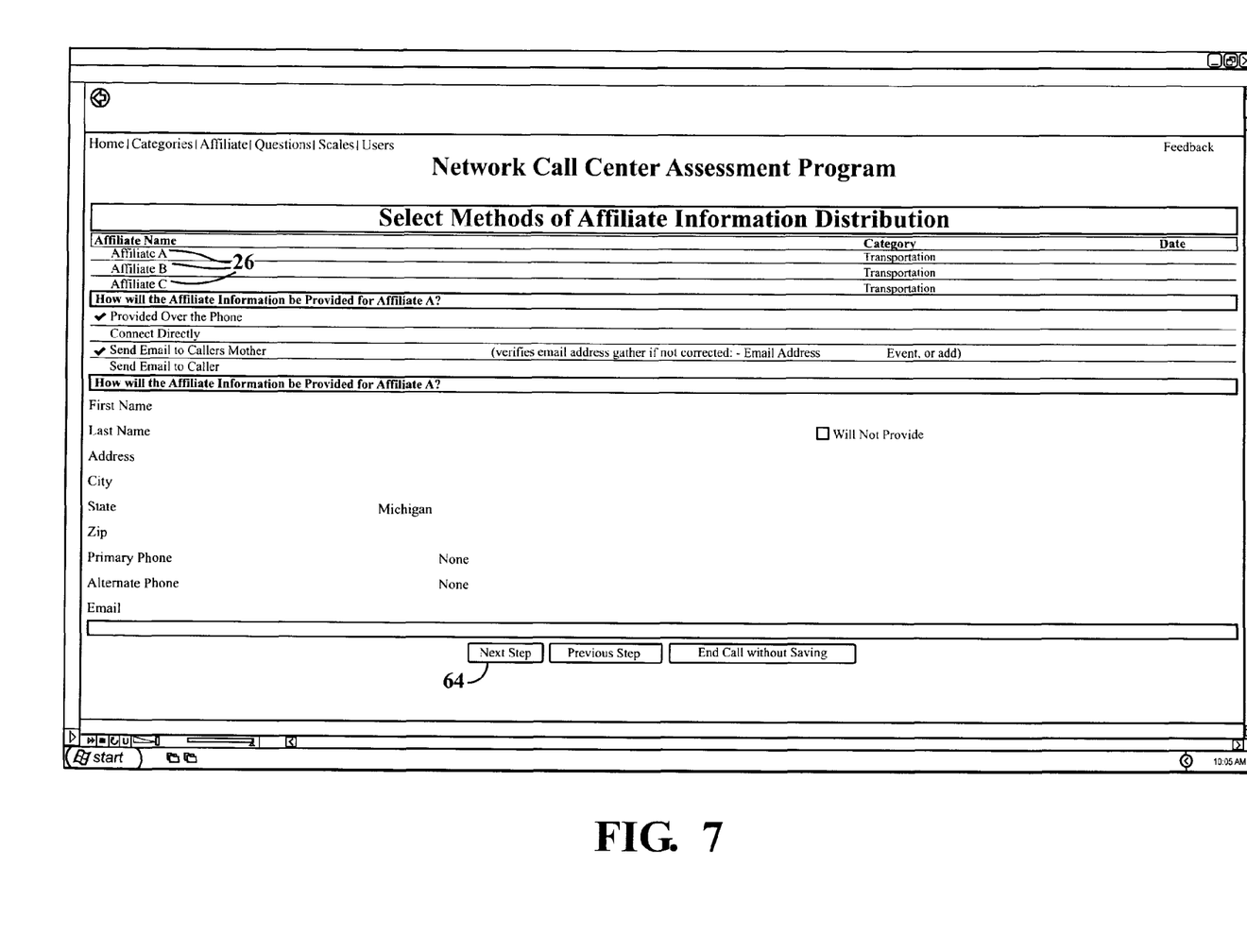
FIG. 7 shows an another exemplary Select Methods of Affiliate Information Distribution window of the exemplary computer program for communicating with the database of the call center network.

In the Select Methods of Affiliate Information Distribution window, the representative 32 can choose which portions of the user information to send to the affiliate 26 and/or how to send the affiliate information to the user. The database 24 can communicate with the user and the affiliates 26 over the PSTN and/or the Internet, such as through an email message. Next, the representative 32 can click on the "Next Step" link 64, which will present the Set Initial Affiliate Follow Up Schedules window shown in FIG. 8.

Figure 8:
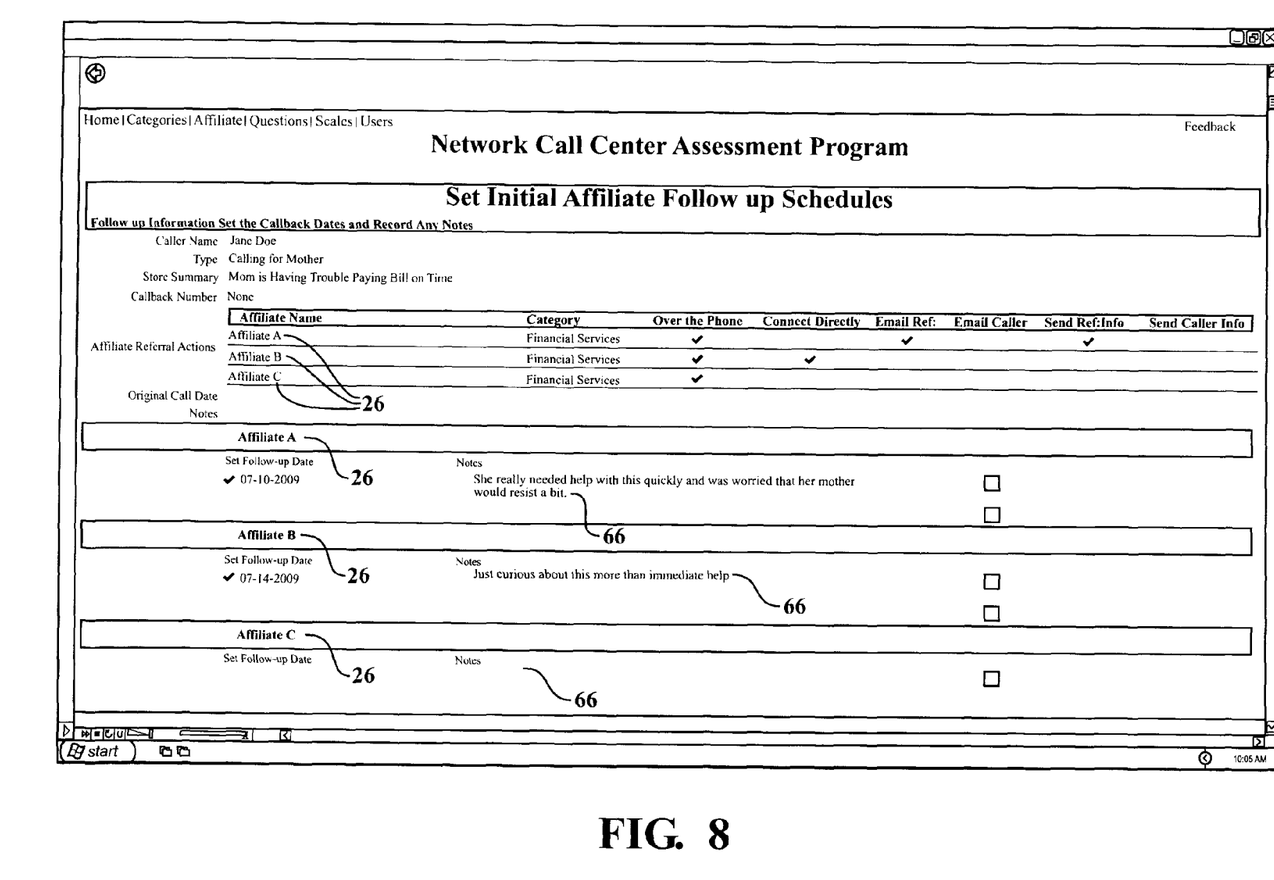
FIG. 8 shows an exemplary Set Initial Affiliate Follow Up Schedule window of the exemplary computer program for communicating with the database of the call center network.

On the Set Initial Affiliate Follow up Schedules window, the representative 32 can choose when and how to follow up with each of the affiliates 26 who received referrals and/or with the user. A space 66 for the representative 32 to enter notes for the follow-up is provided for each of the affiliates 26. The representative 32 can either manually choose when the follow-up communication time will take place, or the follow-up communication can automatically be scheduled for example, one week after the referral.

Figure 9:
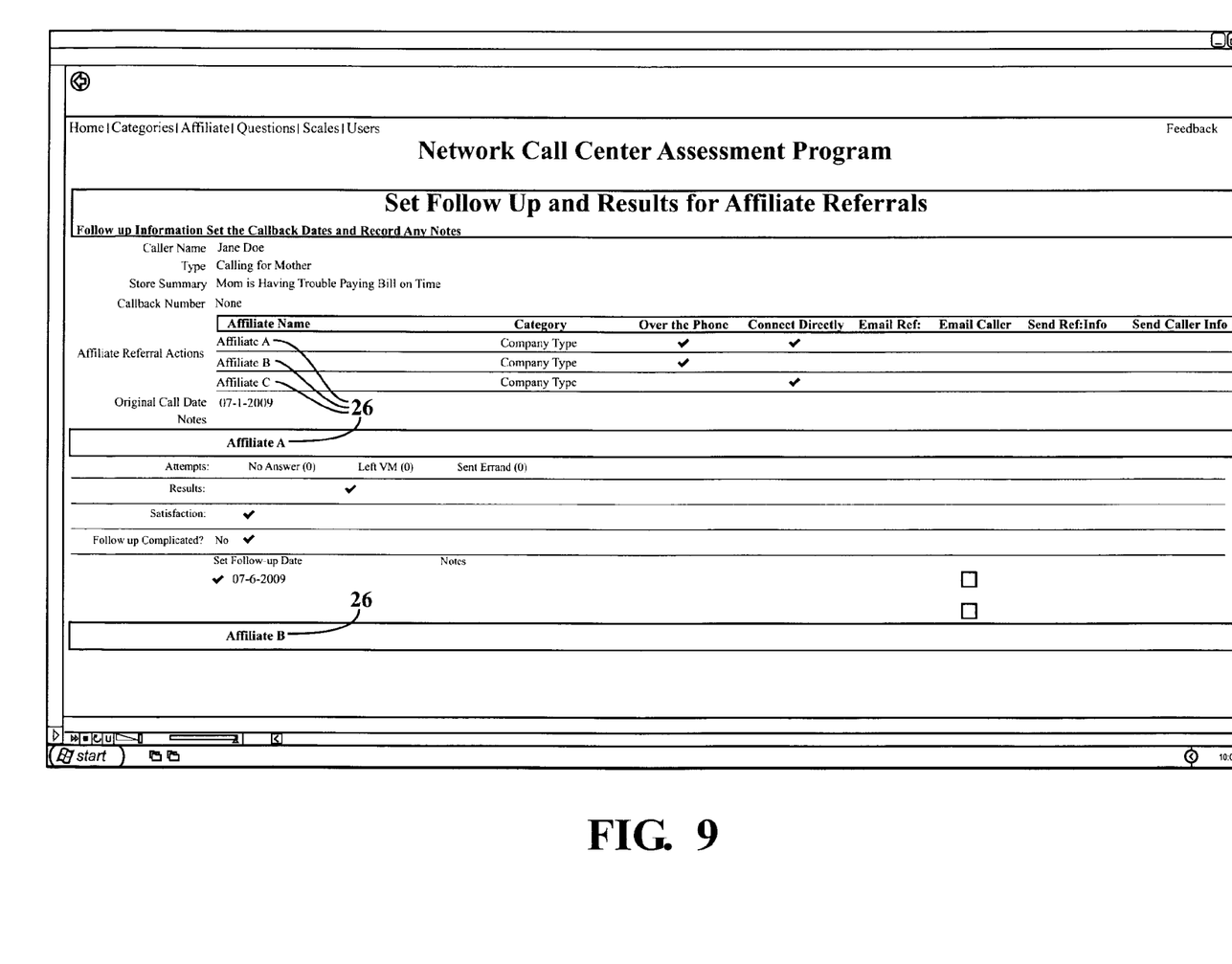
FIG. 9 shows an exemplary Set Follow Up and Results for Affiliate Referrals window of the exemplary computer program for communicating with the database of the call center network.

When a representative 32 does the follow-up communication with the user and/or the affiliate 26, the representative 32 chooses the desired follow-up from the Call Center Assessment Program window of FIG. 2, which presents the Set Follow Up and Results for Affiliate Referrals window shown in FIG. 9. In this window, the representative 32 can input results of the follow-up communication, including a performance value, which could be based on the satisfaction of the user for the service provided by the affiliate 26. This performance value can then be used in the calculation of the relevance scores when the database 24 presents future lists of affiliates 26 for all of the users of the network system 20. The representative 32 can also enter other notes from the follow-up communication into the database 24. If the service has not been performed or is still on-going at the time of the follow-up communication, the representative 32 can schedule an addition follow-up communication. If the call center 22 includes a manager 30, it may be the manager's 30 duty to double check that the representatives 32 are following through with their follow-up communications.

Figure 10A:
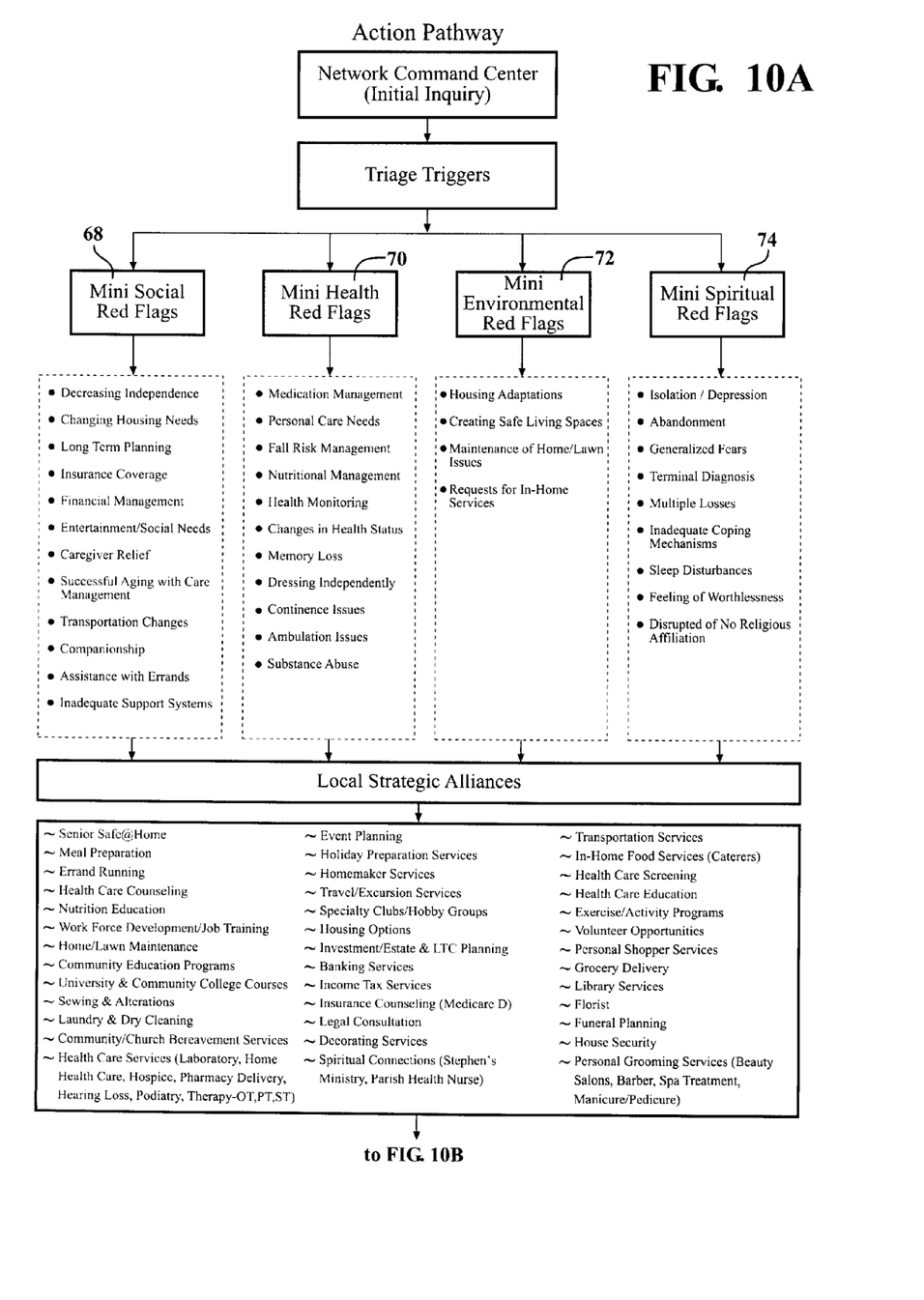
FIG. 10 shows an exemplary pathway of triggers for available information.
Figure 10B:
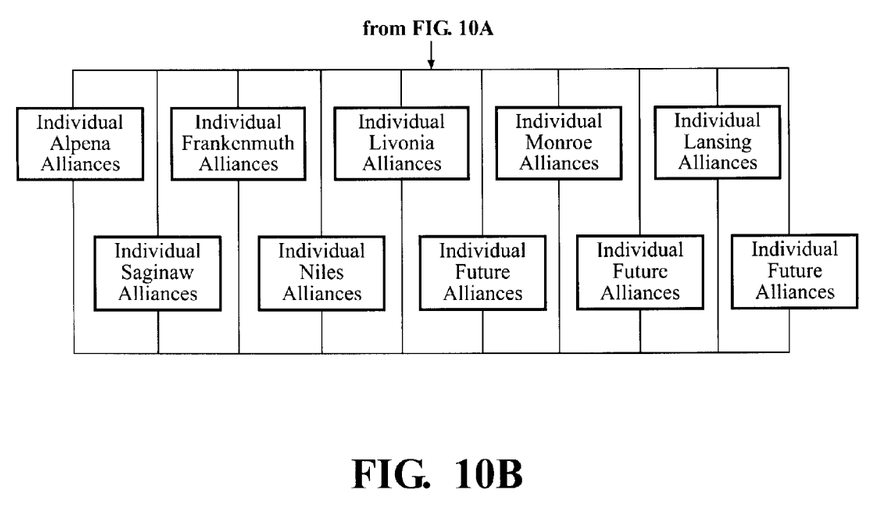

FIG. 10 illustrates an exemplary pathway of triggers for available information. These pathways may be followed during a communication between the user and the representative 32, as described above. The exemplary embodiment includes four mini red flags categories: a Mini Social Red Flag 68, a Mini Health Red Flag 70, a Mini Environmental Red Flag 72 and a Mini Spiritual Red Flag 74. In one example, a user may initially inquire about health issues. The inquiry regarding health issues would trigger the Mini Health Red Flag 70. Mini Health Red Flags may include, for example, medication management, personal care needs, fall risk management, nutritional management, health monitoring, changes in health status, memory loss, dressing independently, continence issues, ambulation issues and substance abuse. Based on these flags, the database 24 aligns with affiliates 26 which will coordinate with the customer to get the appropriate care. For example, if the flag "health monitoring" is determined to be appropriate, the customer may be connected with a "health care counseling" affiliate 26.

The networking system 20 is beneficial because it provides the users with the ability to "age in place" at home. In other words, the users can provide communicate with the call center 22 whenever they do not know what they need or where they need to get it. Further, because of the follow-up process, the anxiety associated with issues of trust that the user might otherwise feel is mitigated. The call center 22, in association with its various affiliates 26, provides a one-stop information and referral service for users, caregivers and families. Solutions are provided after listening to the user's needs, and contacts are made with reputable, high-quality organizations that can assist with the goods and/or services needed. Finally, each customer receives a follow-up communication to ensure that all of his or her needs have been satisfied and that the appropriate quality of service was provided by the affiliates 26.

Figure 11:
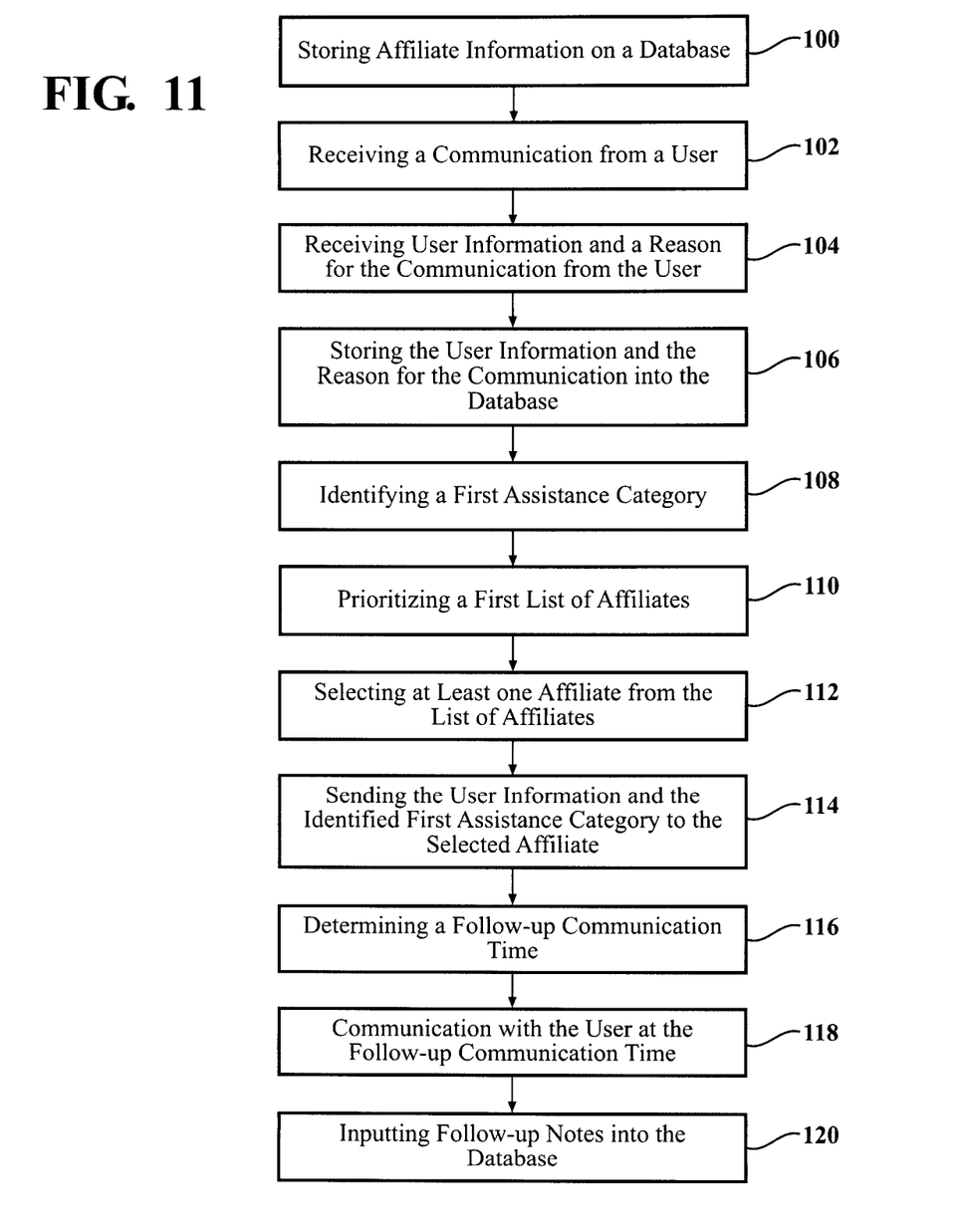
FIG. 11 is a flow chart of the exemplary method of assisting a user.

FIG. 11 shows a flow chart of an exemplary method of assisting a person. The method starts with the step 100 of storing affiliate information for a plurality of affiliates 26 on a database 24. Next, the method continues with the step 102 of receiving a communication from a user. As explained above, the communication from the user could be established by the user walking into a call center 22, by the user calling the call center 22 via telephone, or by the user connecting with the call center 22 over the Internet. The method then continues with the step 104 of receiving user information and a reason for the communication from the user. The user information could include the user's name, contact information, location, etc. The method proceeds with the step 106 of storing the user information and the reason for the communication into the database 24.

Once the user information and the reason for the communication is stored in the database 24, the method continues with the step 108 of identifying a first assistance category. Then the method continues with the step 110 of prioritizing a first list of affiliates 26 as a function of the affiliate information of the plurality of affiliates 26 and the first assistance category identified and the user information. The prioritized first list of affiliates 26 could also be determined as a function of performance values for the affiliates 26 (described in further detail above); the distance between the affiliates 26 and the user; and/or the ability of the affiliates 26 to provide services for multiple assistance categories for the user. Next, the method continues with the step 112 of selecting at least one affiliate 26 from the list of affiliates 26. As discussed above, the user works with a representative 32 to determine which affiliate 26 to choose.

Once the affiliates 26 are chosen, the method continues with the step 114 sending the user information and the identified assistance category to the selected affiliate 26. The user information and the identified assistance category can be sent to the affiliate 26 through any desirable communication channel, including the PSTN and the Internet.

Next, the method continues with the step 116 of determining a follow-up communication time. The method then proceeds with the step 118 of communicating with the user at the follow-up communication time. The follow-up communication time could be any desirable time. The method is finished with the step 120 of inputting follow-up notes into the database 24.

It should be noted that affiliates 26 may be qualified prior to forming relationships with the call center 22. For example, it might be desirable for all of the affiliates 26 to provide free estimates, guaranteed services, a positive better bureau check, the ability to respond to any referral in less than twenty-four hours, daily monitored email accounts, a guarantee that they will not exceed written estimates by more than 10% without written approval, state compliance, etc. Other requirements might be that the affiliate's 26 employees all have a company photo ID, a uniform with company logo and a company marked vehicle to ensure safety. It is further noted that, although FIG. 10 describes prioritizing a first list of the affiliates 26 based on a first assistance category, aspects of the present invention are not limited to this, and it is understood that the affiliates 26 can be prioritized into multiple lists based on one or multiple assistance categories. For example, the method can generate first list of affiliates 26 based on a first assistance category, a second list of affiliates based on a second assistance category, etc. Any combination of prioritizing affiliates based on any combination of assistance categories and/or other information (e.g., user information, location to affiliates, performance values, etc.) is possible according to aspects of the present invention, as would be understood by those skilled in the art.

The described embodiments of the inventions are intended to be merely exemplary and numerous variations and modifications will be apparent to those skilled in the art. All such variations and modifications are intended to be within the scope of the present invention.

What is claimed is:

1. A method of assisting a user, comprising:
storing affiliate information for a plurality of affiliates on a database;
receiving a communication from a user;
receiving user information and a reason for the communication from the user;
storing the user information and the reason for the communication into the database;
identifying a first assistance category in response to the communication;
prioritizing a first list of affiliates as a function of the affiliate information of the plurality of affiliates, the identified first assistance category and the user information;
selecting at least one affiliate from the prioritized first list of affiliates;
sending the user information and the identified first assistance category to the selected affiliate;
determining a follow-up communication time;
communicating with the user at the follow-up communication time; and
inputting follow-up notes related to the selected affiliate into the database based on a communication with the user at the follow-up communication time.

2. The method of assisting a person as set forth in claim 1, further including assigning a performance value to the selected affiliate based on the follow-up notes.

3. The method of assisting a person as set forth in claim 2, wherein the prioritizing of the first list of affiliates includes prioritizing the first list of affiliates as a function of the performance value assigned to the selected affiliate.

4. The method of assisting a person as set forth in claim 1, wherein the storing of the affiliate information on the database includes storing information related to goods and services provided by each affiliate.

5. The method of assisting a person as set forth in claim 4, further including identifying a second assistance category in response to the communication.

6. The method of assisting a person as set forth in claim 5, wherein the prioritizing of the first list of affiliates includes prioritizing the first list as a function of the ability of the affiliates to satisfy the first and second assistance categories.

7. The method of assisting a person as set forth in claim 5, further including prioritizing a second list of affiliates as a function of the affiliate information of the plurality of affiliates and the second assistance category identified and the user information.

8. The method of assisting a person as set forth in claim 1 wherein the storing of the affiliate information on the database includes storing the location of each affiliate.

9. The method of assisting a person as set forth in claim 8, wherein the receiving of the user information includes receiving a location of the user.

10. The method of assisting a person as set forth in claim 9, wherein the prioritizing of the first list of affiliates includes prioritizing the first list as a function of the distance between the user and the affiliates.

11. The method of assisting a person as set forth in claim 1 wherein the identifying of the first assistance category comprises automatically identifying with the database the first assistance category as a function of the reason for the communication from the user.

12. The method of assisting a person as set forth in claim 1, wherein the receiving of the reason for the communication from the user includes receiving answers from the user in response to a plurality of predetermined questions.

13. The method as set forth in claim 1, wherein the receiving of the communication from the user comprises receiving the communication from the user over the public switched telephone network.

14. The method as set forth in claim 1, wherein the receiving of the communication from the user comprises receiving the communication from the user over the Internet.

* * * * *